United States Patent
Hidaji

[19]

[11] Patent Number: 6,099,124
[45] Date of Patent: Aug. 8, 2000

[54] OPHTHALMOLOGICAL SYSTEM AND METHOD

[76] Inventor: Faramarz Hidaji, 5680 Rolling Ridge Rd., Indianapolis, Ind. 46220

[21] Appl. No.: 09/460,789

[22] Filed: Dec. 14, 1999

[51] Int. Cl.[7] ........................................................ A61B 3/14
[52] U.S. Cl. .......................... 351/202; 351/175; 351/209
[58] Field of Search ..................................... 351/200, 201, 351/202, 203, 209, 175, 246, 159, 158, 210; 359/554, 557

[56] References Cited

U.S. PATENT DOCUMENTS

| | | | |
|---|---|---|---|
| 3,844,641 | 10/1974 | Nowak | 351/33 |
| 3,942,862 | 3/1976 | Furukawa et al. | 350/16 |
| 4,105,302 | 8/1978 | Tate, Jr. | 351/210 |
| 4,118,109 | 10/1978 | Crawford et al. | 350/285 |
| 4,418,993 | 12/1983 | Lipton | 352/57 |
| 4,673,263 | 6/1987 | Onufryk | 351/158 |
| 4,753,526 | 6/1988 | Koester | 351/219 |
| 4,818,097 | 4/1989 | Linde | 351/203 |
| 4,856,891 | 8/1989 | Pflibsen et al. | 351/210 |
| 5,270,857 | 12/1993 | Oizumi et al. | 359/554 |
| 5,293,187 | 3/1994 | Knapp et al. | 351/210 |
| 5,360,971 | 11/1994 | Kaufman et al. | 250/221 |
| 5,365,941 | 11/1994 | Yoshimatsu et al. | 128/745 |
| 5,426,499 | 6/1995 | Kosaka et al. | 356/39 |
| 5,448,349 | 9/1995 | Kosaka | 356/73 |
| 5,461,513 | 10/1995 | Maruyama | 359/837 |
| 5,486,948 | 1/1996 | Imai et al. | 359/462 |
| 5,517,021 | 5/1996 | Kaufman et al. | 250/221 |
| 5,548,378 | 8/1996 | Ogata et al. | 355/208 |
| 5,579,171 | 11/1996 | Suzuki et al. | 359/687 |
| 5,629,988 | 5/1997 | Burt et al. | 382/276 |
| 5,654,752 | 8/1997 | Yamazaki | 348/208 |
| 5,731,897 | 3/1998 | Suzuki | 359/557 |
| 5,969,790 | 10/1999 | Onufryk | 351/175 |

FOREIGN PATENT DOCUMENTS

| | | | |
|---|---|---|---|
| 0 301 790 A2 | 7/1987 | European Pat. Off. | A61B 5/00 |
| 0 301 790 A3 | 7/1987 | European Pat. Off. | A61B 5/00 |
| 0 468 340 A2 | 7/1990 | European Pat. Off. | G06F 3/00 |
| 0 468 340 A3 | 7/1990 | European Pat. Off. | G06F 3/00 |
| WO 83/03191 | 3/1982 | WIPO . | |
| WO 91/13584 | 2/1990 | WIPO . | |

*Primary Examiner*—George Manuel
*Attorney, Agent, or Firm*—Woodard, Emhardt, Naughton, Moriarty & McNett

[57] ABSTRACT

An ophthalmological system and method is disclosed having an eye movement sensor. The eye movement sensor provides an output signal. A computer processor processes a signal and provides a signal output. The signal output is utilized to actuate movement of a prism assembly, typically including two or more prism elements located in front of the patient's eye and movable with respect to each other. Prisms are moved in an offsetting prismatic effect with respect to the eye movement to provide corrective vision from rapid involuntary eye movement such as nystagmus and strabismus.

28 Claims, 11 Drawing Sheets

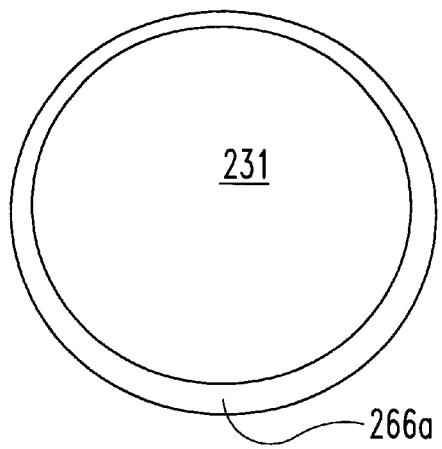
Fig. 11
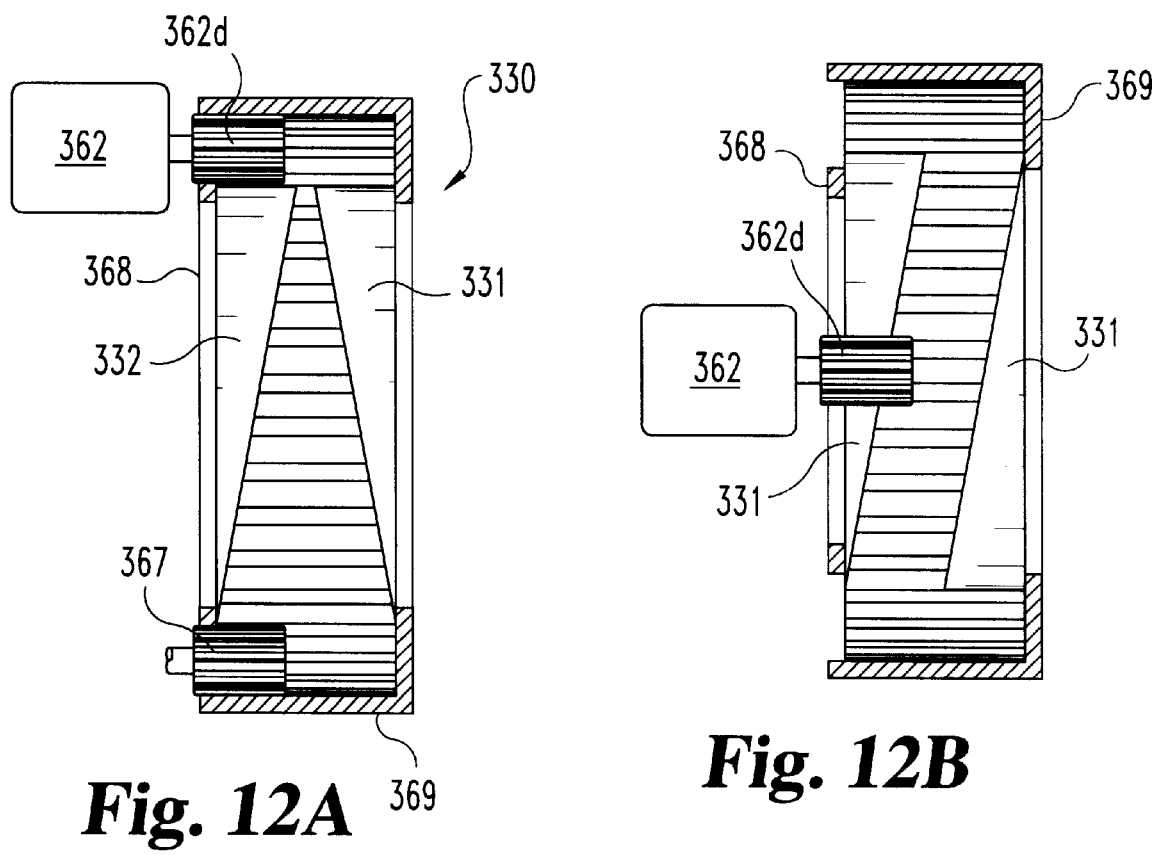
Fig. 12A  Fig. 12B

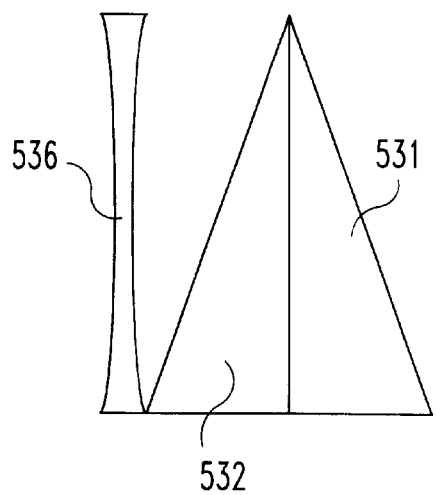
Fig. 14
Fig. 13
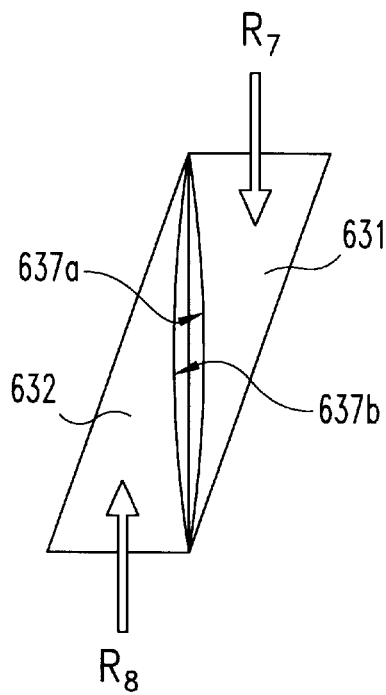
Fig. 15

OPHTHALMOLOGICAL SYSTEM AND METHOD

BACKGROUND OF THE INVENTION

The present invention relates to a system and method for correcting vision, and more specifically for correcting vision problems resulting from rapid involuntary eye movement such as nystagmus and from eye misalignment (i.e. strabismus).

Medical disorders such as nystagmus and strabismus are serious and potentially disabling afflictions. They involve the rapid, involuntary twitching of one or both of a patient's eyes (nystagmus), or involuntary eye misalignment (strabismus). Such movement or twitching are often caused by involuntary muscular action of the extraocular muscles which are responsible for eye movement. Such involuntary eye movement can occur very rapidly and it often is side to side in the general horizontal plane, although other times may occur with vertical and/or diagonal components. Moreover, such twitching can occur multiple times in rapid succession. Although severity and frequency can vary among patients, the results can include severe degradation of eyesight, loss of balance and motor control and general disorientation.

Such problems are fairly widespread. Some data suggests that approximately one (1) out of ten thousand (10,000) people are born with nystagmus. Moreover, other data suggests that approximately one (1) out of fifteen hundred (1,500) people suffer from nystagmus due to the fact that, in addition to people born with this affliction, other people develop it later in life as a result of accidents or trauma, disease or otherwise.

To date, the glasses and contact lenses, surgical and pharmacological treatments for nystagmus, strabismus, and related ailments are unsatisfactory. Various background is set forth in Cox, Neil, & Rushton, David. (1987), A new optical treatment for oscillopsia, *Journal of Neurology and Psychiatry*, 50, 411–415; Averbuch-Heller, MD, L, & Leigh, MD, R J. (1997), Medical treatments for abnormal eye movements: Pharmacological, optical and immunological strategies, *Australian and New Zealand Journal of Ophthalmology*, 25, 7–13; Leung, Vicki; Wick, Bruce, & Bedell, Harold E., (1996) Multifaceted Treatment of Congenital Nystagmus: A Report of 6 Cases. *Optometry and Vision Science*, 73, No. 2, 114–124; Leigh, MD, R. John; Rushton, MD, David N.; Thurston, MD, Stephen E.; Hertle, MD, Richard W, & Yaniglos, O D, Stacy S., (1988) Effects of retinal image stabilization in acquired nystagmus due to neurologic disease, *Neurology*, 38, 122–127; and in Leigh, R. John & Yaniglos, Stacy S., (1992) Refinement of an Optical Device that Stabilizes Vision in Patients with Nystagmus, *Optometry and Vision Science*, 69, No. 6, 447–450. Patients could benefit significantly from the present invention which provides for a system and method for correcting or improving the vision of such patients.

SUMMARY OF THE INVENTION

The present invention provides a system and method for improving or correcting vision of persons having rapid involuntary eye movement, typically from side to side, up and down and/or both. The invention is set forth in the claims, below, but is generally summarized as optionally including one or more of the following features. A variable prism is located in front of one or more of the patient's eyes which are afflicted. The position of the prism is adjustable to alter the direction of light as it passes through the prism. The present invention also includes a sensing device which senses positioning movement of an afflicted eye. The sensing device provides a signal output correlated to eye movement. Signal output results in a signal input to the adjustable prism. The adjustable prism is adjusted in response to correct or improve vision.

Various versions and embodiments of the foregoing are contemplated. Without limitation, one version of the adjustable prism includes two prism elements adjacent to each other and rotatable with respect to each other. Thus, upon rotation, the angle of refraction relative to this prism is adjustable. Another version of the prism can include a fluid filled adjustable prism which is selectively adjustable to adjust the angle of refraction.

A microprocessor or other computer may preferably be utilized to optimize the performance of the invention. For example, signal processing can include fuzzy logic, artificial intelligence and/or signal filtering to enhance and/or optimize the time and location correlation between adjustment of the prism in response to involuntary eye movement.

One object of the invention is to provide an improved system and method for treating the aforesaid vision problems as claimed.

BRIEF DESCRIPTION OF THE DRAWINGS

FIG. 11 is the front view of a prism element with a counterweight attached thereto;

FIG. 12A is another embodiment of a prism assembly of the present invention having two prism elements in a planetary gear assembly;

FIG. 12B is a top view of the assembly of FIG. 12A with the prism rotated to the null position;

FIG. 13 is a side view of an alternative prism arrangement;

FIG. 14 is a side view of another prism arrangement in combination with a corrective lens;

FIG. 15 is another alternative prism arrangement including corrective lens surfaces integrally ground into the prism element;

DESCRIPTION OF THE PREFERRED EMBODIMENTS

Figure 1:
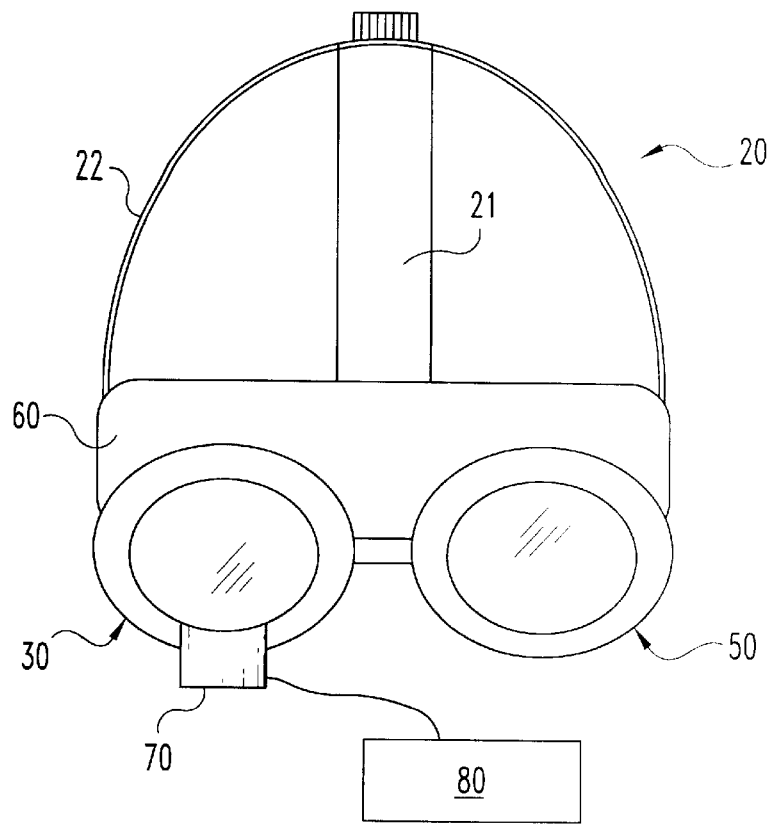
FIG. 1 is a front view of a first embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated system and method, and further applications of the principles of the invention as illustrated therein are herein contemplated as would normally occur to one skilled in the art to which the invention relates.

Figure 2:
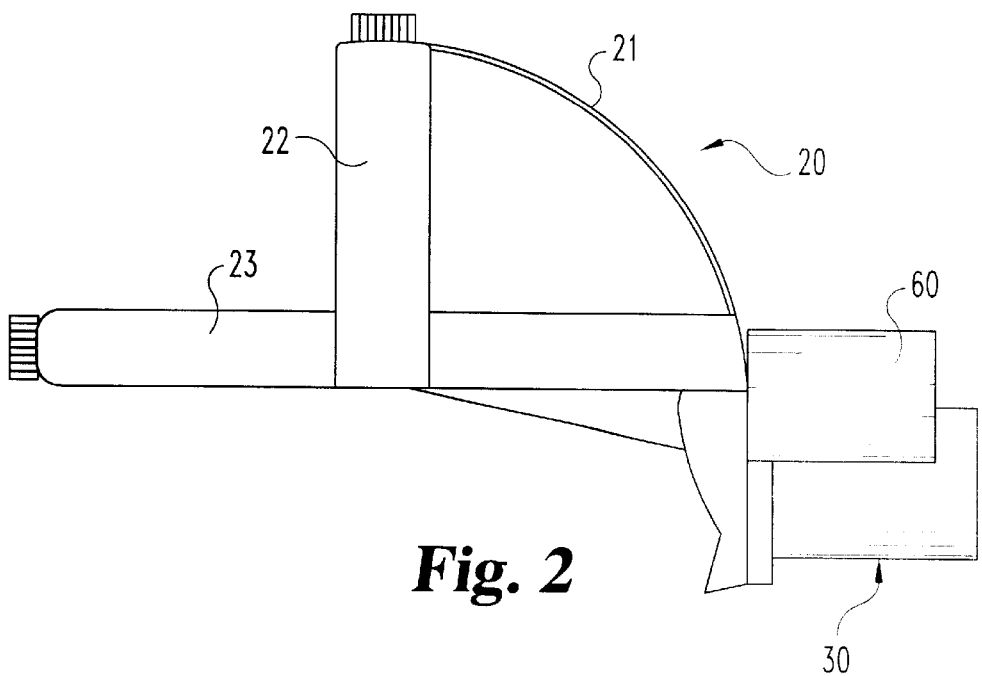
FIG. 2 is a side view of the device of FIG. 1.

Several examples of the present invention are set forth. FIGS. 1 and 2 illustrate the present invention, ophthalmological system 20 including the head mounting gear. Such gear includes band 21, band 22 and band 23. Other head mounting systems may be utilized depending on weight and balance characteristics, including conventional eyeglass ear pieces. System 20 includes the right prism assembly 30 and the left prism assembly 50 as well as an actuator assembly 60. A sensor unit 70 senses rapid involuntary eye movement of the patient's eye. A signal is sent therefrom to processor unit 80 which includes an electrical power source, typically batteries, as well as processing capability such as a microprocessor. As shown in FIG. 1, sensor 70 and processor 80 are connected by suitable wiring, it being contemplated that radio frequency or non-wired systems may optionally used as well for signal transmission.

Figure 3:
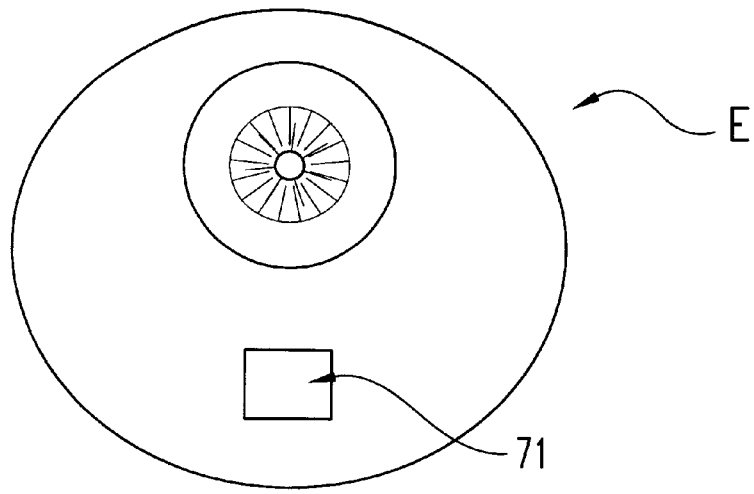
FIG. 3 is a front view of a patient's eye having a sensor mark on the eye.
Figure 4:
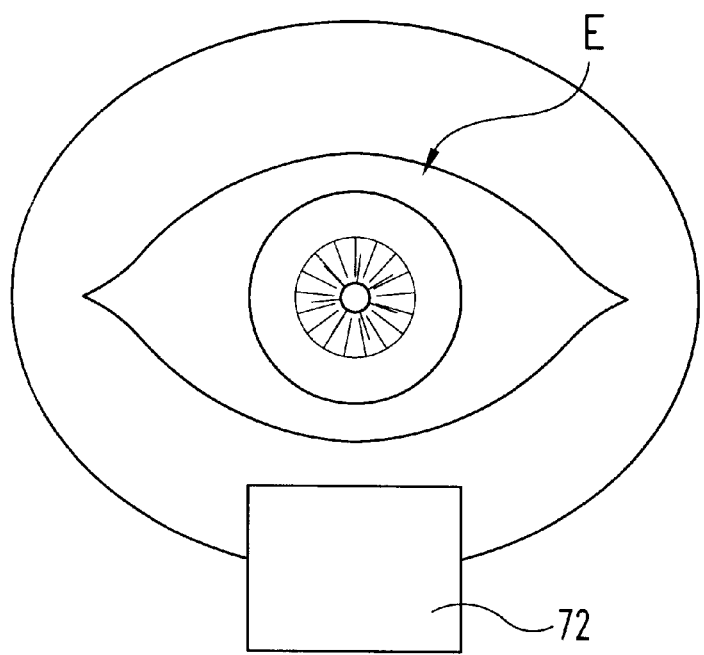
FIG. 4 is a front view of a patient's eye with a sensory device in front thereof to detect rapid eye motion.
Figures 5A, 5B:
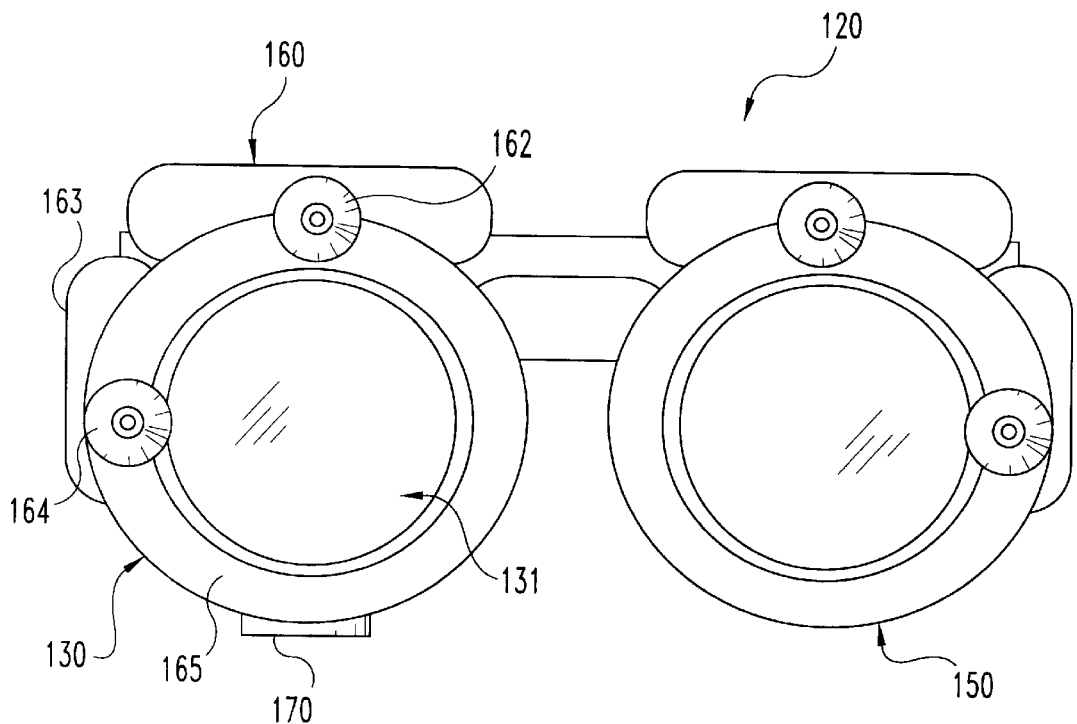
FIG. 5A is a front view of another embodiment of the present invention.
FIG. 5B is a partial top view of the device of FIG. 5A partially cut away.
Figure 6A:
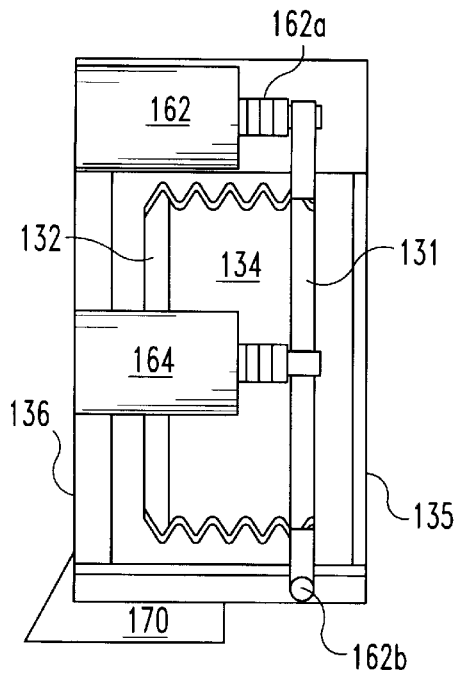
FIG. 6A is a partially cut away side view of a prism assembly portion of the device of FIG. 5A.
Figure 6B:
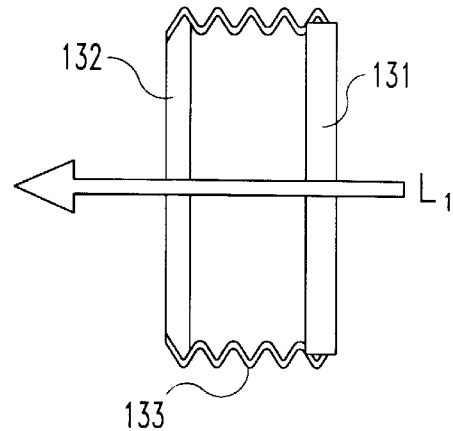
FIG. 6B is a top view of a prism element of the device of FIG. 5A shown in isolation and showing a light ray passing therethrough.

FIGS. 3 and 4 illustrate one of several components and methods used to detect involuntary rapid eye motion. As illustrated in FIG. 3, eye marker 71 is provided directly on the patient's eye E. This may take a variety of forms. In the illustrated example, a ferromagnetic implant is surgically implanted into the eye, preferably at the six o'clock position as illustrated in FIG. 3. Sensor 72, detecting changes in a magnetic field from marker 71, senses the presence, amplitude and timing of rapid eye motion in the patient's eye suffering from nystagmus or similar affliction. This is converted into a analog or digital signal used in connection with the present invention. Such signal is preferably provided as output from the sensor inputted to processor unit 80 described further below. Other forms of detecting eye motion can include the use of a reflective member, instead of a magnetic insert, in which a light beam is reflected off of the member. Rapid eye movement causes fluctuation in the reflected light, again allowing the sensor to detect timing and amplitude of such eye displacement and to provide an output signal. Other markers may be provided, including laser etching on the eye tissue. Anatomy, such as the contrasting pupil, may serve as a marker tracked by the sensor. Moreover, the present invention contemplates determining an eye position change event to actuate the corrective features of the invention discussed below. Such change event most preferably is the type of marker system set forth above. However, it is further contemplated that other physiological detection systems that correspond to the symptoms of a nystagmus or similar affliction may be used. For example, electrode sensors may be attached to the eye muscles which twitch and cause the nystagmus. Such galvanic current may used (amplified, filtered and otherwise) to provide the timing and amplitude signals to provide the sensor output signal for the present invention.

Figure 7A:
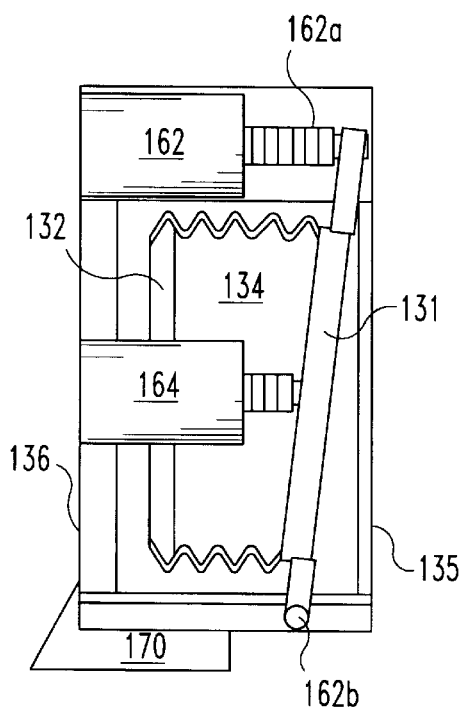
FIG. 7A shows the device of FIG. 6A with the front prism element moved.
Figure 7B:
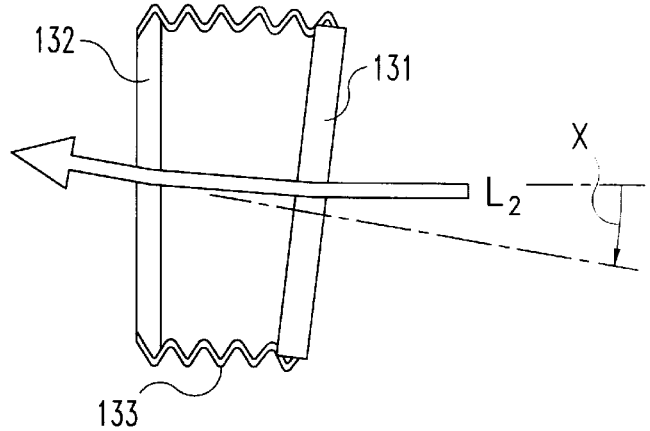
FIG. 7B is a top view of the prism element of FIG. 6B with the front prism element moved and showing a light ray refracted therethrough.

FIGS. 5A–7B disclosed one version of the corrective eyeglasses of the present invention. It is to be understood that this eyeglass system and the others described are interactive with the processing unit 80 and the sensor unit 70 previously described. This ophthalmological system 120 includes at least one prism assembly 130, and most preferably includes a second prism assembly 150 for the left eye. Sensor 170 is as previously described. Note that this embodiment, sensor 170 is only associated with the right eye, it being understood that separate sensors may be provided for each eye to allow either independent operation, or for data averaging in the processing steps for correction since ordinarily nystagmus effects both eyes simultaneously. The prisms used in this embodiment utilize prism technology currently thought to be used in image stabilization binoculars. Such prisms are set forth in U.S. Pat. Nos. 4,418,993, 3,942,862, 5,731,897, 5,654,752, 5,629,988, 5,579,171, 5,270,857, 5,548,378, and 5,461,513 which are hereby incorporated by reference. Front prism element 131 and rear prism element 132 are interconnected by bellows 133. A light transmissive media 134, typically liquid or gel, lies between the two prism elements within the bellows. At least one, and preferably two or more actuators, such as actuator 162 and actuator 164 move prism elements 131 and 132 with respect to each other. For example, as illustrated, actuator 164 has extendable arm 164a which selectively moves in and out based on processor 80 signals. Pivot 164b is located across the prism assembly. Thus, as arm 164a moves in and out, element 131 pivot about 164b. Similarly, as seen by comparing FIG. 6A and 7A and by comparing FIG. 6B and 7B, actuator 162 has arm 162a. Across from the prism is pivot 162b. As illustrated between FIGS. 6A and 6B, as actuator arm 162a extends, prism element 131 pivots on pivot 162b. Prism element 132 in this embodiment is stationary, and accordingly 131 is moved with respect to it. As illustrated in FIG. 6B, prism elements 131 and 132, which are each planer and transparent, are parallel to each other. As such, a light ray $L_1$ passing through them does so without angular refraction, instead passing straight through in what is referred to as the "null" position. By contrast, as shown in FIG. 7B, with prism element 131 angled with respect to element 132, light ray $L_2$ is refracted by an angle X. The light transmissive media between the prism elements is allowed to flow as one side of the bellows expands and the other side contracts, thereby providing an overall prism effect while maintaining minimal chromatic and other optical distortion other than the prism effect.

Figure 16:
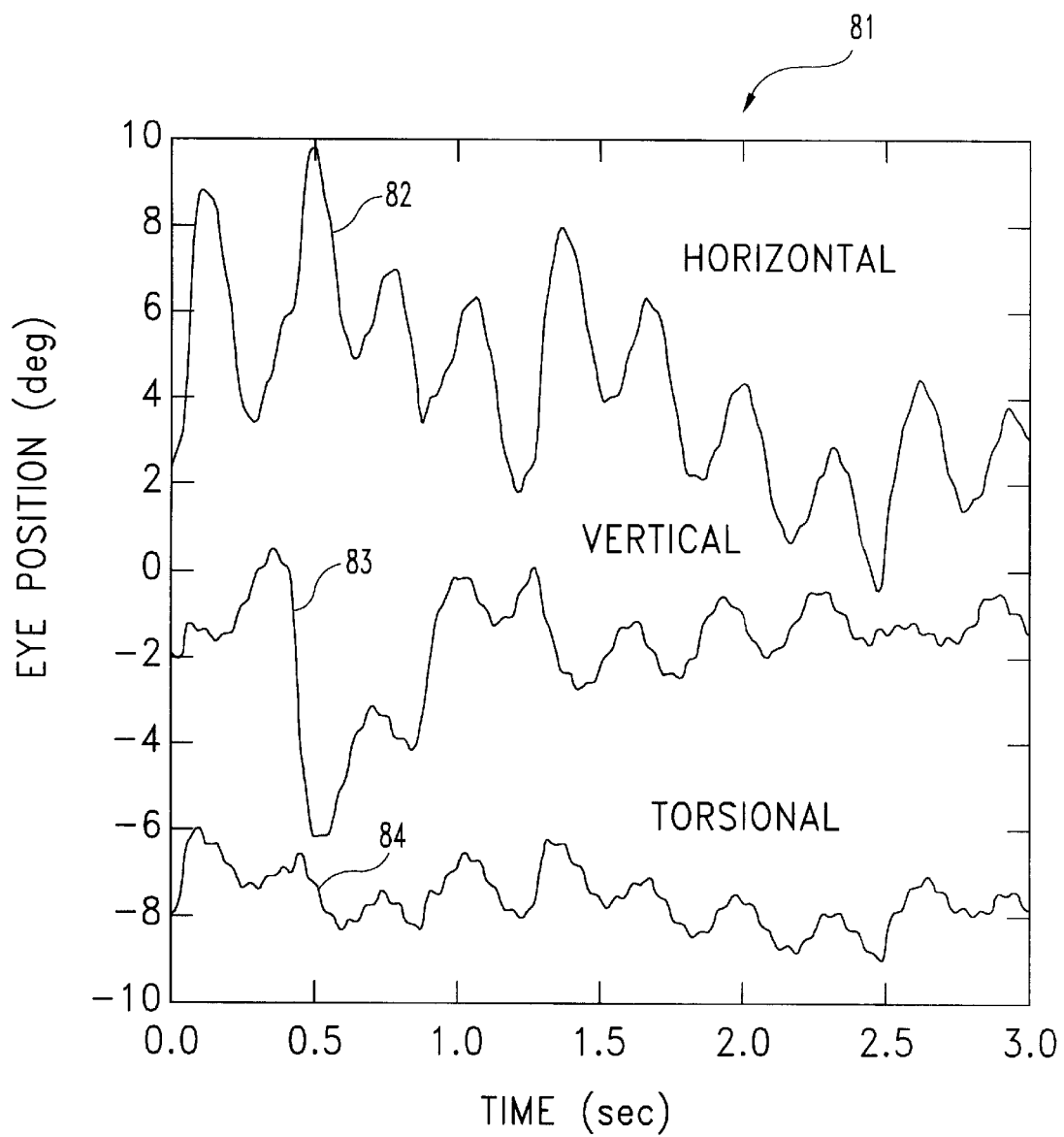
FIG. 16 is a graph reprinted from a prior art publication providing an exemplar horizontal, vertical and torsional angular eye displacement as a function of time; and, FIG. 17 is a flowchart setting forth selected steps according to one way of processing signals for the present invention.

Rapid involuntary eye movement of the type dealt with with the present invention is illustrated in the reprinted graph of FIG. 16. As can be seen, rapid and rather erratic angular eye position changes occur within fractions of seconds. These can occur both horizontally 82, vertically 83 and/or torsionally 84. With sensing apparatus previously described a rapid response time detects such eye displacement. It is to be understood that tracking precision (in time and position) is relative, the greater the tracking capability and prism response movement, the greater the therapeutic value of the corrective effect of the present invention. As such, for example in FIG. 16, as set forth in table 81 in FIG. 16, the horizontal displacement plot 82 is tracked by the sensory unit 170. It provides the signal to the microprocessor unit. The microprocessor unit can have a variety of programming attributes, its main function being to receive angular displacement signals on the sensory unit, and translate them essentially real time to output signals to correspondingly oppositely move the prisms an angular amount corresponding to the nystagmus driven displacement, and thereby substantially offsetting the effect of the rapid eye position change. This may utilize a combination of programming and plotting techniques. This may include extrapolation of the input data, preprogrammed curve profiles triggered by initial sensory input (e.g. speed and acceleration), as well as simple direct translation of sensory displacement and therapeutic displacement of the prisms. The prism/eye coordinates may be processed in Cartesian coordinates, polar coordinates or otherwise. Moreover, software may be used including fuzzy logic and/or artificial intelligence systems which store in memory eye movement patterns for a particular patient and iteractive modify the therapy output signal for each patient. The output is provided typically as an electrical signal to the actuators. For example, the electrical signal can be provided to actuator 162 cause actual movement of arm 162a and prism element 131 by an angle X as illustrated in FIG. 7A and 7B. This would correspond to vertical angular displacement, such as shown in plot 83 in FIG. 16. Thus, if sensor 170 detected at a point in time a rapid involuntary eye movement displacement of 5 degrees, the signal would be processed by processor unit 80 and a corresponding signal would be sent to actuator 162 and move element 131 to effective prismatic effect offsetting an angle X (see FIG. 7B) of corresponding minus 5 degrees in the same plane. This would be preferably done real time, or with any lag time or lead time minimized to optimize visual acuity. Similarly, as illustrated in vertical position plot 83 (FIG. 16), as eye position returned to the null position, similarly actuator arm 162 would retract so that prism elements 131 and 132 were parallel (see FIG. 6B) and likewise be in the null position.

It should be noted that preferably the present invention is optionally configured to disregard slower voluntary eye movement. In this way, the patient may voluntarily look up or down or off to one side without having therapeutic effects of the prisms automatically triggered. This may be done a variety of ways, for example, a filtering circuit may be used or in the processor 80 programming, filtering programs may be utilized to filter out and disregard slower eye movement or acceleration not typically associated with nystagmus. Alternatively, a temporary override switch may be provided the user can manually suspend operation of the system by the push of a button or otherwise.

Figure 17:
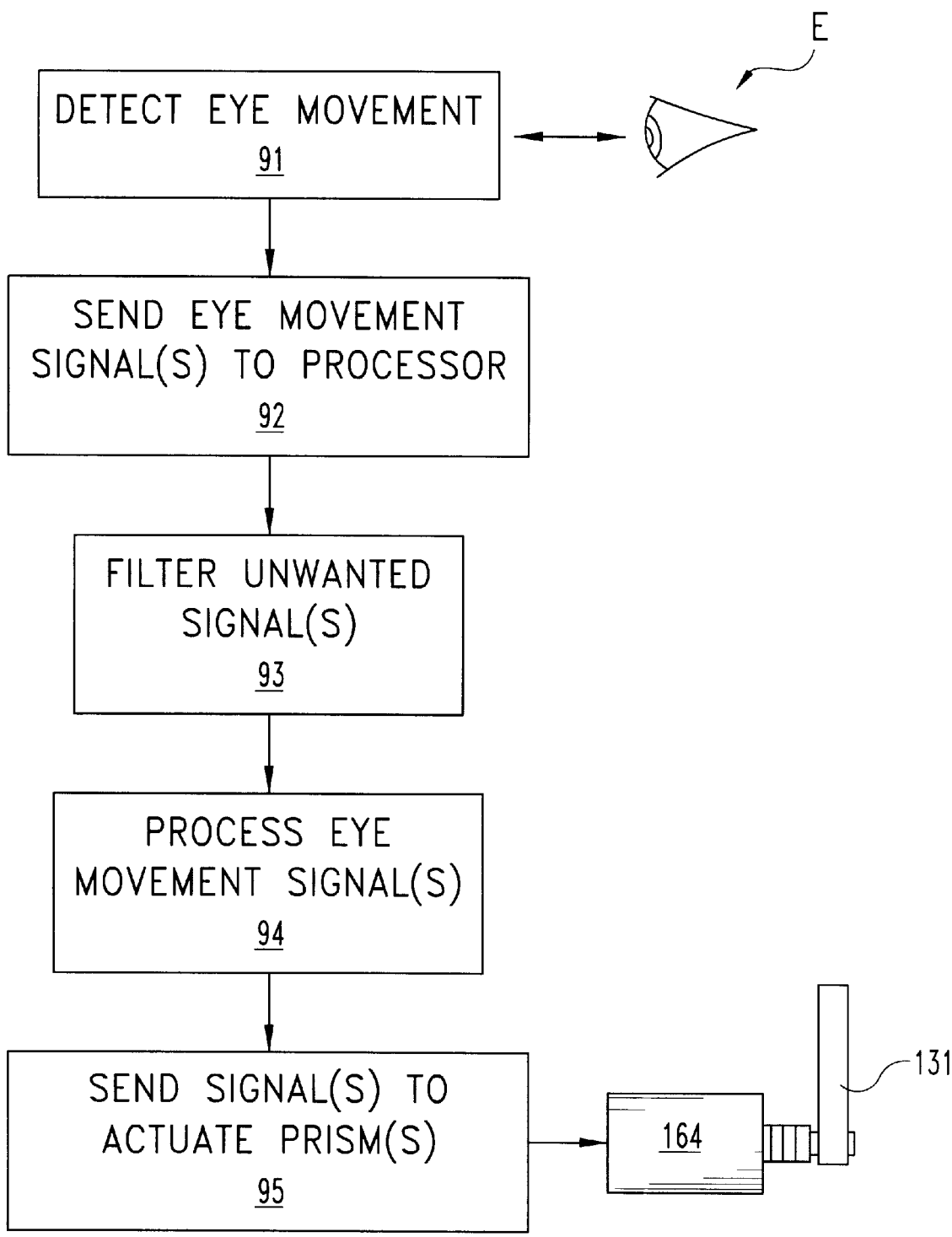

As shown in FIG. 17, detection of eye movement of the eye E occurs at box 91. This results in sending an eye movement signal 92 to the processor 80. Typically unwanted signals are filtered at 93. This may include disregarding slower voluntary eye movement as discussed above. Note further that the filtering in box 93 may be considered a sub-part of the processing box 94 which processes the eye movement signals from the detected eye movement. After such processing step 94, the processor sends actuator signals in box 95 to actuate the prisms. For example, such sending of signal 95 is illustrated in FIG. 17 to be directed to actuator 164 to move prism element, it being understood that any of the other actuators contemplated by this invention may likewise be used.

It is further understood that the filtering at 94 is optional and not always required for the invention. Moreover, while not preferred, it is possible to have eye movement detection system which has a signal output which is directly readable by actuator device in a calibrated corresponding fashion. This alternatively can involve the use of linear amplifiers and/or logic circuits between the sensor and the prism actuators. In such case, intermediate computer processing would not always be required.

Figure 8A:
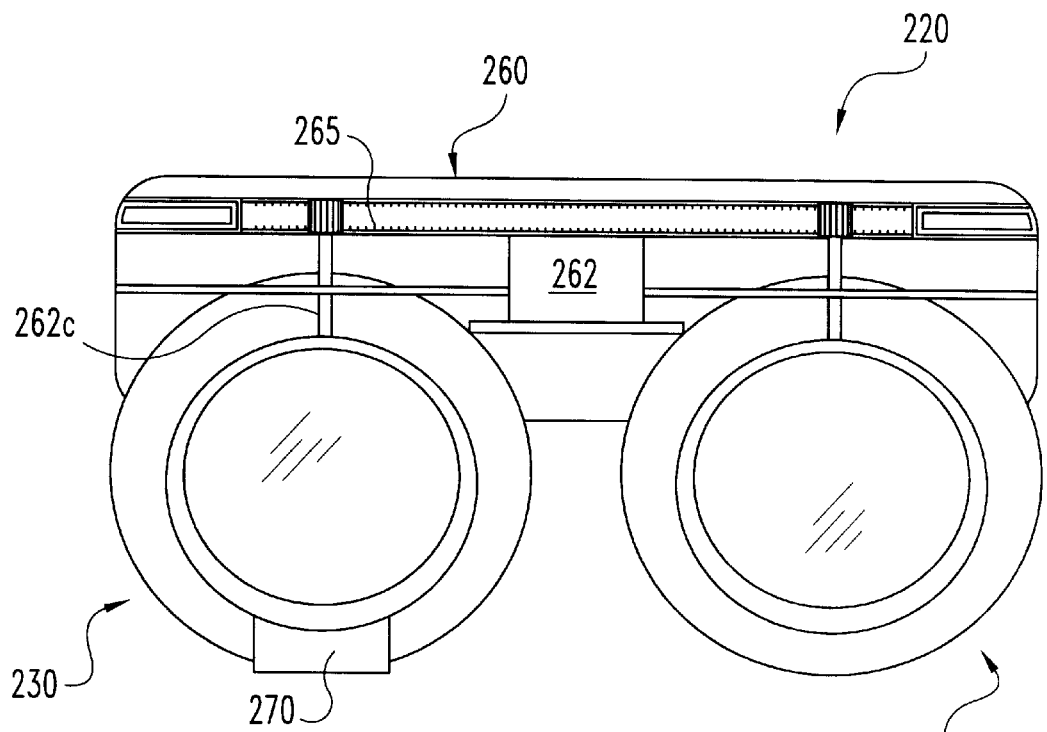
FIG. 8A is a front view of another embodiment of the present invention.
Figure 8B:
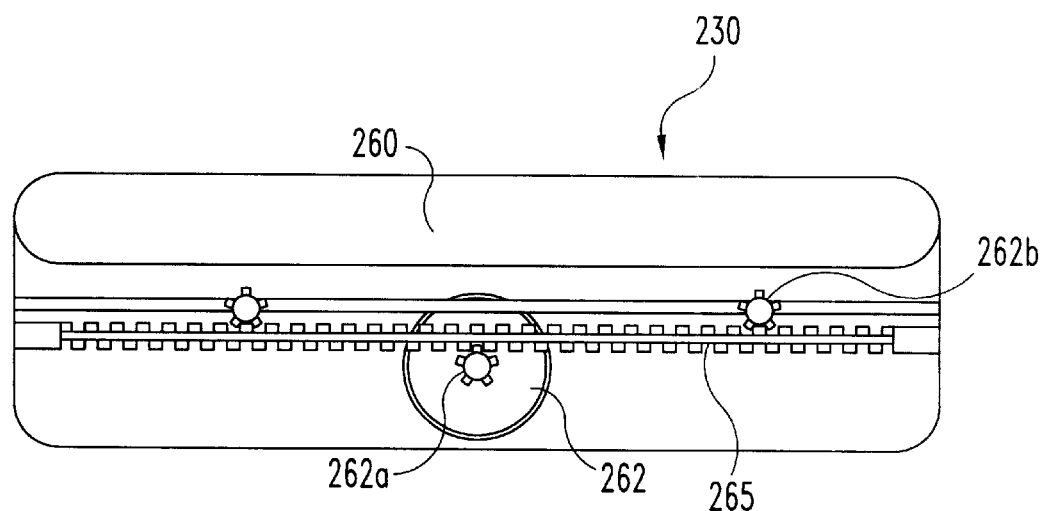
FIG. 8B is a partial top view of the device of FIG. 8A.
Figure 8C:
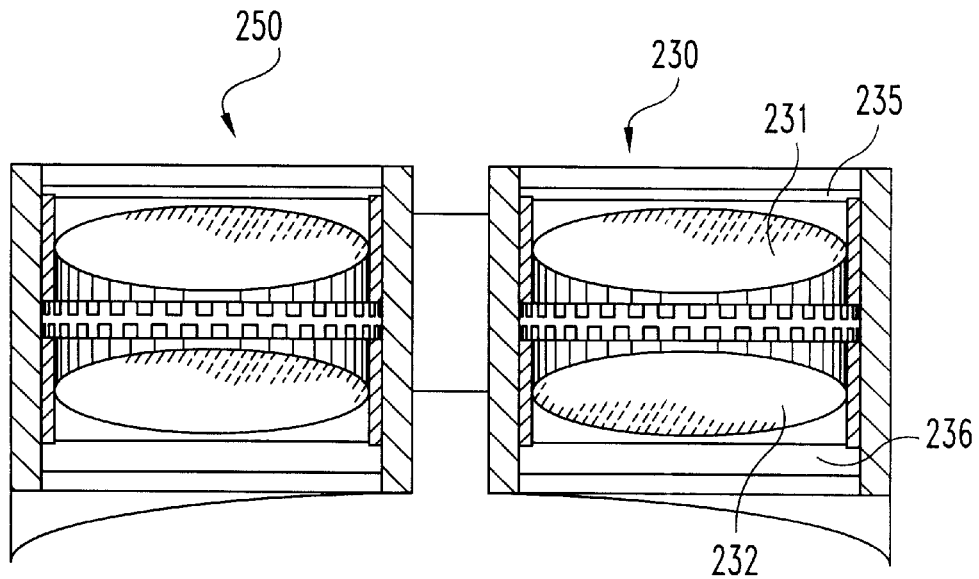
FIG. 8C is a partially cut away top view of the device of FIG. 8A showing the two prism assemblies.
Figure 8D:
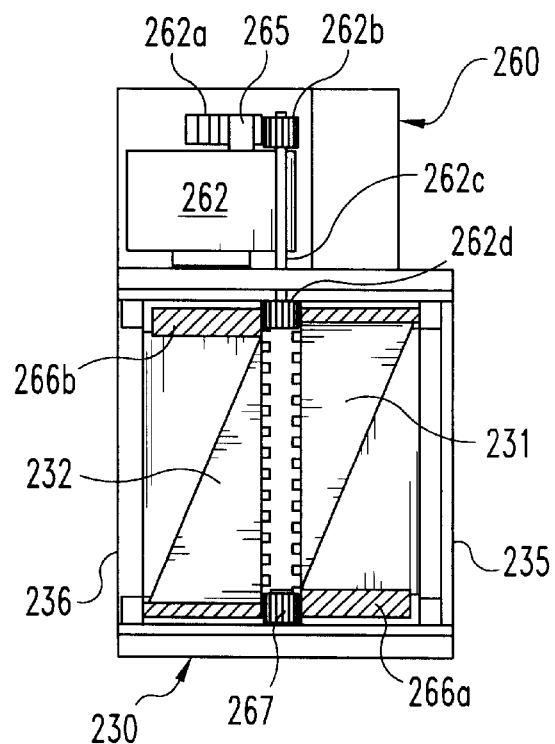
FIG. 8D is a partially cut away side view of the device of FIG. 8A showing prisms in the null position.
Figure 9A:
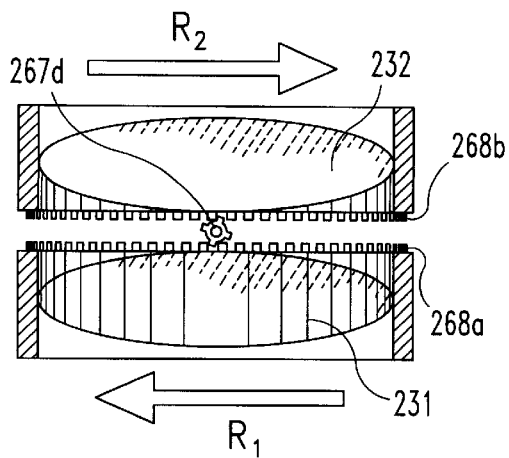
FIG. 9A is a top view of a prism assembly of FIG. 8D in isolation in the null position.
Figure 10A:
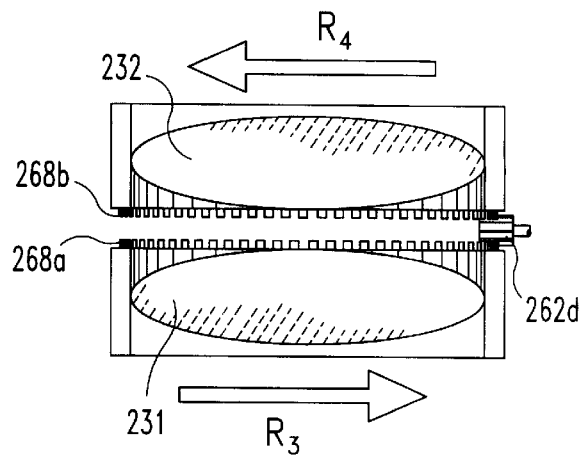
FIG. 10A is a side view of a prism assembly of FIG. 8D in isolation to provide maximum refraction.
Figure 9B:
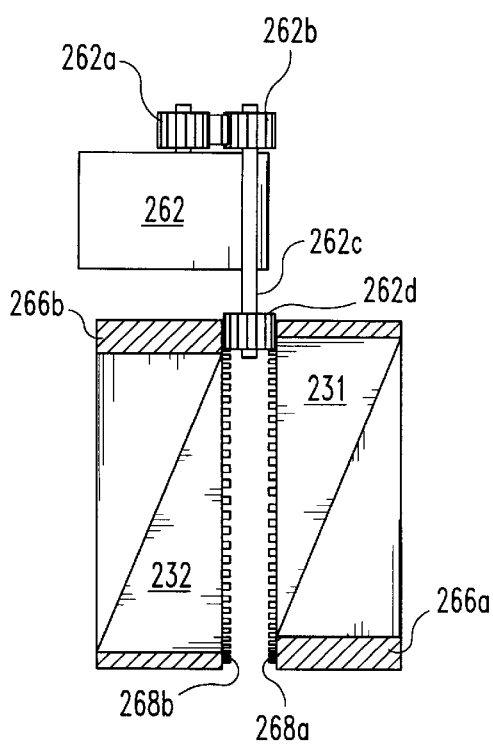
FIG. 9B is a partial side view in isolation of the prism components of FIG. 8D rotated with respect to each other to provide no refraction.
Figure 10B:
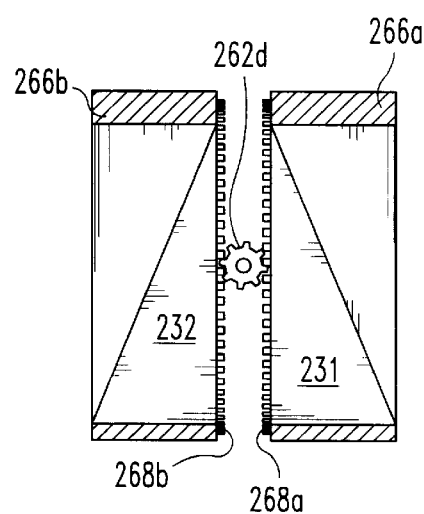
FIG. 10B is a partial top view in isolation of the prism components of FIG. 9B.

Other optical corrective systems may be utilized with the present invention in connection with the sensory components and the processing of the sensory output data. For example, a pair of prisms, rotatable with respect to each other may be utilized to provide therapeutic angular prismatic effect. The device of FIGS. 8A–10B is one such ophthalmological system 220. The system includes a right prism assembly 230 and a left prism assembly 250 and an actuator assembly 260. The prism elements 231 and 232 are each frustocylindrical. They are circular when viewed from the front (see FIGS. 8A, 11) and are right triangles when viewed from the side (see e.g. FIGS. 8D, 9B, 10). When these prism elements 231 and 232 are in the null position (as shown in FIGS. 8D and 9B) their refractive effects offset each other. Thus, although each of them by virtue of their shape has a prismatic effect, they cancel each other out with the net effect that the prism assembly 230 is null and the prism faces are parallel to each other, forming effectively a parallelogram as illustrated in FIG. 8D. However, when elements 231 and 232 are rotated 180 degrees with respect to each other, as illustrated in FIG. 10A and 10B, a maximum combined refractive effect is achieved since the light refractive attribute of prism element 231 is combined with the prismatic effect of prism element 232. Thus, for given prism angle this relative position provides the maximum angular displacement of light. It should be noted, that this can be achieved by maintaining one prism element stationary and rotating the other prism element diametrically 180 degrees, or alternatively may be achieved by rotating each separate prism element 90 degrees in opposite directions. This twin 90° rotation reduces the total travel distance for a given prism element, thereby economizing on mechanical movement while counterbalancing rotational inertia of the two prism elements.

In this regard, one optional feature may be the utilization of the counterbalance weight 266a on prism element 231 and counterbalance 266b on element 232. This is best seen in FIG. 8D and FIG. 11, with the counterbalance being a displaced weigh diametrically across from the thickest portion of the prism element. Ideally, it is configured gradually around the circumference of the prism with an increase in mass of the counterbalance corresponding to a decrease in thickness (and therefore mass) of the prism. This way, the combined counter-balance and prism is more radially symmetric with respect to the central axis of rotation of the prism, thereby eliminating wobbling forces during rotation.

Mechanical rotation of the prisms can be achieved in any way. As illustrated in the example of ophthalmological system 230, a motor drive and gear system may be used. For example, a single actuators, such as motor 262, such as a stepper motor, servo motor or the like are actuated in response to output signals (typically from processor 80) to provide the drive impetus to move the prisms. The gear rack 265 engages gear 262a from the actuator 262. The gear rack, having gears on both faces, likewise engages gear 262b attached to axle 262c which is likewise attached to gear 262d. Rotation of this gear 262d engages prism gear teeth 268a and 268b, causing the prisms to rotate in opposite directions such as rotation $R_2$ and $R_1$ (see FIG. 9A) and on the return trip, rotation $R_3$ and $R_4$ (see FIG. 10A).

FIGS. 12A and 12B illustrate an alternative gearing arrangement. In this configuration, a planetary gear assembly is provided to provide counter rotation of prism element 331 with respect to prism element 332. Prism element 332 is mounted to an externally geared mount 368. Prism element 331 is mounted to an internally geared mount 369. A motor drive 362 is provided with gear 362d located in between outer geared mount 368 and inner geared mount 369. Thus, with associated motor drive rotation, one of the prisms rotates clockwise while the other rotates counterclockwise. Preferably two or more stabilizing planetary gear member 367 are provided to hold assembly in concentric relationship between the prism elements. Thus, as illustrated in FIG. 12A, the prismatic effect of prism elements 331 and 332 is maximized. Shown in FIG. 12B, with the prisms rotated their prismatic faces parallel to each other, they offset each others prismatic effect, thereby providing the entire prism assembly with a null effect. Gear housing 368 and gear housing 369 (FIGS. 12A and 12B) have a concentric opening in each of them, with the prism being mounted thereto only around the perimeter so as to allow light to pass through the prism assemblies.

It should be noted that, particularly for patients with whom the amplitude of eye movement fluctuates significantly, sometimes being great, and other times being small, the prisms, motor drive systems and associated computer processor programming may be configured for initial rotation, and then counter rotation. Initial rotation responds to the initial angular displacement away from the null position, and the counter rotation returns back to the null position by rotating in the opposite direction.

An alternative approach can be used. This approach may be used for patients for whom the amplitude of angular displacement is generally consistent. In such case, the prism element angles are prescribed to jointly correspond with the maximum angular eye displacement amplitude for that patient. In this case, mechanical advantages can be achieved by continuing the rotation in the same direction both during the initial displacement phase as well as the return to the null phase. In other words, by continually rotating the prisms with respect to each other in a constant direction, a sinusoidal profile of prismatic effect is achieved. This sinusoidal profile frequency can be modified real time by the processor input to correspond with non-idealized sinusoidal curve characteristics of the patient's eye displacement and associated speeding or slowing of the drive motor(s). Nevertheless, by modeling the sinusoidal curve profile one advantage is achieved by conserving rotational inertia of the rotating prisms, rather then starting and stopping the prisms for each cycle.

As mentioned, gear drives are only one approach rotating prisms. Belt drives, friction drives and any other mechanical rotational mechanism to rotate one or both of the prism elements may be utilized with the present invention.

FIGS. 13, 14 and 15 schematically illustrate a variety of alternative prism and/or lens configurations, from the side view, it being understood that these prism elements are mounted in one of the prism rotation assemblies linked up to the processor and sensory features of the invention previously described. FIG. 13 has prism element 431 and prism element 432 in engagement along their flat circular surface. Rotation occurs at such abutting interface by counterclockwise rotation $R_5$ and clockwise rotation $R_6$.

FIG. 14 illustrates a configuration similar to the FIG. 13, although the prism elements have been rotated to maximize the net prismatic effect between prism element 531 and 532. Furthermore, FIG. 14 illustrated an optional feature which is corrective element 536. It should be noted that such corrective element may be utilized with any of the embodiments of the present invention so as to correct other vision problems with the patient. Corrective element 536 may include concave, convex and other ground lenses, typically according to the eyeglass prescription of the patient such as, for example, to correct nearsightedness, far-sightedness, astigmatism and the like.

FIG. 15 illustrates another approach with prism element 631 and adjacent prism element 632 for counter rotation $R_7$ vis-a-vis rotation $R_8$. Corrective surface 637a is ground in element 631, and corrective surface 637b is ground in prism element 632. In this way, prescription correction be ground directly into the prism.

An alternative correction embodiment may be used as well. Rather than transparent prisms, the use of the close circuit video camera may be used with the video screens placed close proximity in front of the eyes, such as on the inside surface of eyeglasses. Preferable, this would be a digital video camera with digital image. As the eye sensor 70, previously described, detects unwanted eye motion, such as from nystagmus, and the signals are processed by processor 80, the position registry had the digital image and the glasses is proportionally shifted in the same direction as the eye is moving at or about the same timing. Such real time digital image shift would provide the virtual appearance of a stationary image to the patient.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Claimed references to "a" and similar singular reference are open and include devices having two or more such elements as well.

What is claimed is:

1. A system for improving a patient's vision from involuntary movement of the patient's eye position caused by involuntary eye muscle movement, comprising:
    a variable prism positionable in front of the patient's eye, the angle of refraction of said prism with respect to the eye being variable in response to signal input; and,
    a sensor for determining an eye position change event, said sensor providing a signal output for said signal input to correspondingly counter-vary said angle of refraction of said variable prism.

2. The system of claim 1 and further comprising signal processing means to process said signal output as corresponding to eye movement into said signal input to cause corresponding angles of refraction of said variable prism.

3. The system of claim 2 including an electrical actuator to move said prism.

4. The system of claim 3 comprising two variable prism assemblies, a left prism assembly and a right prism assembly locatable in front of the patient's left and right eye, respectively.

5. The system of claim 4 wherein said variable prism has at least one actuator which extends and retracts to move a pair of prism surface members in different planes with respect to each other.

6. The system of claim 5 and further including a liquid between said two prism surfaces.

7. The system of claim 6 and further comprising a non-planer corrective lens surface positionable in front of the patient eyes to provide vision correction.

8. The system of claim 5 wherein said variable prism includes a first prism element and a second prism element selectively rotatable with respect to said first prism element to vary their collective prismatic effect.

9. The system of claim 8 and further comprising a gear and motor drive assembly for actuating movement of said variable prism.

10. The system of claim 8 and further comprising a prism element which is heavier on one side than an opposite side and further comprising a counter-weight attached to said prism element generally opposite said heavier side to to provide counter-balancing during movement of said prism element.

11. The system of claim 4 wherein said sensor includes a magnetic marker on the patient's eye.

12. The system of claim 4 wherein said sensor includes a light reflective marker attachable to the patient's eye and an associated light-receptive sensor to detect movement.

13. The system of claim 4 and further comprising a non-planer corrective lens surface positionable in front of the patient eyes to provide vision correction.

14. The system of claim 1 including an electrical actuator to move said prism.

15. The system of claim 1 comprising two variable prism assemblies, a left prism assembly and a right prism assembly locatable in front of the patient's left and right eye, respectively.

16. The system of claim 1 wherein said variable prism has at least one actuator which extends and retracts to move a pair of prism surface members in different planes with respect to each other.

17. The system of claim 16 and further including a liquid between said two prism surfaces.

18. The system of claim 1 wherein said sensor includes a magnetic marker attachable to the patient's eye.

19. The system of claim 1 wherein said sensor includes a light reflective marker on the patient's eye and an associated light-receptive sensor to detect movement.

20. The system of claim 1 wherein said variable prism includes a first prism element and a second prism element selectively rotatable with respect to said first prism element to vary their collective prismatic effect.

21. The system of claim 1 and further comprising a gear and motor drive assembly for actuating movement of said variable prism.

22. The system of claim 1 and further comprising a prism element which is heavier on one side than an opposite side and further comprising a counter-weight attached to said prism element generally opposite said heavier side to to provide counter-balancing during movement of said prism element.

23. The system of claim 22 and further comprising a non-planer corrective lens surface positionable in front of the patient eyes to provide vision correction.

24. A system for improving a patient's vision from involuntary movement of the patient's eye position caused by involuntary eye muscle movement, comprising:

variable means positionable in front of the patient's eye for varying a light image with respect to the eye in response to signal input; and, sensor means for determining an eye on position change event and providing a signal output for said signal input to correspondingly vary a light image; and, signal processing means to process said signal output as corresponding to eye movement into said signal input to cause said light image variations.

25. A method for improving a patient's vision from involuntary movement of the patient's eye position caused by involuntary eye muscle movement, comprising:

sensing in real time rapid eye position change; and, moving an optical element in real time in front of the patient's eye in general synchronicity with said eye position change to substantially offset the effect of said rapid eye position change.

26. The method of claim 25 including processing an electrical signal corresponding to said sensing, said processing providing an output electrical signal to an actuator to cause said moving of said optical element.

27. The method of claim 26 wherein said moving includes moving a first prism element with respect to a second prism element from a parallel null position to a non-parallel refractive position.

28. The method of claim 26 wherein said moving includes rotating a first prism element with respect to a second prism element.

\* \* \* \* \*